United States Patent [19]

Mase et al.

[11] Patent Number: 4,797,194

[45] Date of Patent: Jan. 10, 1989

[54] ELECTROCHEMICAL ELEMENT

[75] Inventors: Syunzo Mase, Tobishima; Shigeo Soejima, Nagoya, both of Japan

[73] Assignee: NGK Insulators, Ltd., Nagoya, Japan

[21] Appl. No.: 171,225

[22] Filed: Mar. 22, 1988

Related U.S. Application Data

[63] Continuation of Ser. No. 899,815, Aug. 25, 1986, abandoned.

[30] Foreign Application Priority Data

Aug. 30, 1985 [JP] Japan ................................ 60-192568

[51] Int. Cl.$^4$ ............................................ G01N 27/46
[52] U.S. Cl. .................................. 204/425; 204/426; 204/427; 204/429; 264/56; 264/61
[58] Field of Search ........................... 204/15, 421–429

[56] References Cited

U.S. PATENT DOCUMENTS

| | | | |
|---|---|---|---|
| 4,051,009 | 9/1977 | Schweickart et al. | 204/279 |
| 4,450,065 | 5/1984 | Yamada et al. | 204/426 |
| 4,498,968 | 2/1985 | Yamada et al. | 204/426 |
| 4,502,939 | 3/1985 | Holfelder et al. | 204/428 |
| 4,505,806 | 3/1985 | Yamada | 204/425 |
| 4,505,807 | 3/1985 | Yamada | 204/425 |

FOREIGN PATENT DOCUMENTS 140028 3/1979 Norway ........................ 204/1 R

Primary Examiner—T. Tung
Attorney, Agent, or Firm—Parkhurst, Oliff & Berridge

[57] ABSTRACT

An electrochemical element including a planar solid electrolyte body, and at least pair of electrodes including a first electrode and a second electrode which are disposed on the planar solid electrolyte body. The element has a thin flat space which has a predetermined diffusion resistance to a measurement gas and which communicates with an external space in which the measurement gas exists. The first electrode is disposed so that it is substantially exposed to the measurement gas in the thin flat space. The element includes a bridging member which is interposed between two opposed flat surfaces which partially define the thin flat space. The bridging member substantially determines the thickness of the thin flat space. The bridging member is formed by firing a mixture consisting of a filler material which disappears upon firing thereof, and ceramic grains which are fired into the bridging member. The mixture is applied in the form of a layer so as to occupy at least a portion of the thin flat space to be formed.

32 Claims, 8 Drawing Sheets

ELECTROCHEMICAL ELEMENT

This is a continuation of application Ser. No. 899,815 filed Aug. 25, 1986 now abandoned.

BACKGROUND OF THE INVENTION

1. Field of the Invention

The present invention relates to an electrochemical element and a process of manufacturing the same. More particularly, the invention is concerened with an improved construction of an electrochemical element using a solid electrolyte to determine the concentration of a component of a gas, which construction is effective to minimize a variation in quality from one element to another. The invention is also concerned with a process suitable for producing an electrochemical element of the above type having such an improved construction.

2. Discussion of the Related Art

There has been known an electrochemical device with an electrochemical element using a solid electrolyte, for example used as an A/F ratio sensor for determining the oxygen concentration of an exhaust gas emitted by an internal combustion engine of an automotive vehicle, or determining the concentration of unburned components of the exhaust gas. An example of this type of electrochemical sensor includes an electrochemical cell with an oxygen-ion conductive solid electrolyte of zirconia ceramics and a pair of porous electrodes, capable of performing an electrochemical pumping action due to the electrode reaction with an electric current flowing between the two electrodes. One of the two electrodes is exposed to an external gas to be measured, through a suitable diffusion-resistance means such as a thin flat space or a porous ceramic layer which has a predetermined diffusion resistance to the molecules of the external gas. A pumping current flowing between the two electrodes is used as an output of the sensor which represents the oxygen concentration of the external gas to be measured, or the concentration of the unburned components of the gas. Also known is an electrochemical detector or device similar to the A/F ratio sensor described above, which is operated to deal with water or detect hydrogen, carbon dioxide, etc., according to the principle of an electrochemical pumping action and a diffusion resistance to the molecules of a component of the gas to be measured.

A typical example of the electrochemical element discussed above is disclosed in U.S. Pat. No. 4,450,065, wherein an electrode disposed on a planar zirconia solid electrolyte layer is exposed to a gas in a thin flat space or gap which has a predetermined diffusion resistance and which communicates with an external space in which the gas exists. The atmosphere adjacent to the exposed surface of the electrode is controlled such that the diffusion resistance of the thin flat space limits an amount of diffusion of the gas through the thin flat space to the exposed surface of the electrode. This electrode cooperates with another electrode to effect an electrochemical pumping action. Further, the electrode exposed to the thin flat space cooperates with yet another electrode also exposed to the thin flat space, in order to achieve an electrochemical sensing operation for sensing an electric current applied across the two pumping electrodes, and thereby detecting the concentration of a component of the gas.

In the electrochemical element with such an arrangement as indicated above the diffusion resistance of the thin flat space communicating with the external measurement gas space is generally determined by a construction or configuration and dimensions of the thin flat space, in particular by the gap amount or thickness of the thin flat space. Attempts have been made to form such a thin flat space so that its thickness or gap is substantially constant over its entire area from the inlet of the gas to its extremities remote from the inlet.

According to the investigation by the present inventors, however, the diffusion resistance of the thin flat space or gap in communication with an external measurement gas space tends to have a considerably large variation from one electrochemical element to another, where the element is produced in a large lot. In other words, the present inventors found it difficult to produce the electrochemical elements with substantially the same diffusion resistance, i.e., with consistent operating characteristics. Thus, a conventional process of manufacturing an electrochemical element suffers difficulty in obtaining a desired value of diffusion resistance of the thin flat space. This difficulty arises from a tendency that solid electrolyte layers, electrode protective layers or other members which define a thin flat space will warp or sag at their portions defining the inlet or open end of the flat space, during a firing process, due to different shrinkage factors of the individual components of the electrochemical element. Such deformation of the members defining the thin flat space results in significant inconsistency of the configuration of the thin flat space from one element to another.

For the production on a commercially justifiable basis of consistently high quality electrochemical elements of the type having a thin flat space communicating with an external measurement gas space, it is important to minimize a variation in the diffusion resistance of their thin flat space from one element to another. Up to the present, however, no efforts have been made to form the thin flat space with a predetermined constant thickness, and thereby minimize a variation in their diffusion resistance.

SUMMARY OF THE INVENTION

It is therefore an object of the present invention to provide an electrochemical element with a thin flat space, which has meas for permitting the thin flat space to provide a diffusion resistance exactly as intended.

Another object of the invention is to provide a process of manufacturing electrochemical elements with a thin flat space, which is effective to minimize a variation in the diffusion resistance of the thin flat space from one element to another.

According to the invention, there is provided an electrochemical element, comprising: (a) a planar solid electrolyte body; (b) at least pair of electrodes including a first electrode and a second electrode which are disposed on the planar solid electrolyte body; (c) means for defining a thin flat space which has a predetermined diffusion resistance to a measurement gas and which communicates with a measurement-gas space in which the measurement gas exists, the first electrode being substantially exposed to the measurement gas in the thin flat space, the means for defining a thin flat space including two opposed flat surfaces perpendicular to a plane of the thin flat space; and (d) ceramic bridging means disposed in the thin flat space, for bridging a gap between the two opposed flat surfaces and thereby substantially determining a thickness of the thin flat space.

According to one advantageous feature of the invention, the first electrode is spaced a predetermined distance away from an inlet of the thin flat space through which the measurement gas is introduced into the thin flat space. The ceramic bridging means is disposed at least in an area of the thin flat space corresponding to the above-indicated predetermined distance.

According to another advantageous feature of the invention, one of opposite major surfaces of the planar solid electrolyte body on which the first electrolyte is disposed comprises one of the two opposed flat surfaces of the means for defining a thin flat space. In this case, the electrochemical element may further comprise another solid electrolyte body having a major surface which comprises the other of the two opposed flat surfaces of the means for defining a thin flat space. According to an alternative feature of the invention, the element further comprises a protective layer disposed so as to cover the first electrode on the planar solid electrolyte body, and one of opposite major surfaces of the protective layer remote from the first electrode comprises one of the two opposed flat surfaces of the means for defining a thin flat space. In this case, the element may further comprise another layer made of a material similar to that of the protective layer, and one of opposite major surfaces of the above-indicated another layer on the side of the protective layer comprises the other of the two opposed flat surfaces of the means for defining a thin flat space. In either case, the means for defining a thin flat space may preferably comprise two members which have the two opposed flat surfaces and which are made of substantially the same material. Preferably, the ceramic bridging means may be made of the same material as the material of the above-indicated two members.

According to a further advantageous feature of the invention, the ceramic bridging means consists of a plurality of mutually spaced-apart ceramic members which are disposed at least in an area of the thin flat space adjacent to an inlet of the thin flat space through which the measurement gas is introduced into the thin flat space. In one preferred form of the invention, the ceramic bridging means consists of a plurality of ceramic grains having a diameter which is substantially equal to the thickness of the thin flat space.

The thin flat space formed in the element so as to provide the predetermined diffusion resistance may directly communicate, at its inlet, with the external measurement-gas space. Alternatively, the thin flat space may communicate with the measurement-gas space via a gas inlet aperture having a suitable cross sectional area. In either case, the thin flat space may be advantageously formed between a first electrochemical cell which are constituted by the planar solid electrolyte body and first and second electrodes which are described above, and a second electrochemical cell which are constituted by another planar solid electrolyte body and another pair of electrodes.

According to the present invention, the electrochemical cell constructed as described above is suitably manufactured in a process which comprises: (a) preparing a mixture which consists of a filler material which disappears upon firing thereof, and ceramic grains or particles; (b) applying the mixture in the form of a layer having a predetermined thickness, so as to occupy at least a portion of the thin flat space to be formed; (c) firing the layer of the mixture so that the filler material disappears and contributes to forming a part of the above-indicated portion of the thin flat space, while the ceramic grains are fired into the ceramic bridging means which connects the two opposed flat surfaces to each other and substantially determines the thickness of the thin flat space over an entire area of the thin flat space from an inlet thereof to extremities thereof remote from the inlet.

According to one advantageous feature of the method of the present invention, the two opposed flat surfaces defining the thin flat space are formed by two ceramic members of substantially the same material which are fired at a suitable firing temperature. The ceramic grains are fired into the ceramic bridging means at a temperature lower than the firing temperature of the above-indicated two ceramic members.

In the electrochemical element and the process according to the present invention which has been described, the thickness of the thin flat space is determined or defined by the ceramic bridging means which bridges the gap between the two opposed flat spaces that partially define the thin flat space. In other words, the ceramic bridging means effectively protects the thin flat space from being deformed, thus permitting the thin flat space to provide a diffusion resistance which is as close as possible to the predetermined value. Thus, a variation in the diffusion resistance from one element to another may be significantly reduced.

In summary, the present invention provides effective minimization of a variation in the diffusion resistance of the thin flat space of the electrochemical elements, and thus allows commercially justifiable large-lot production of the electrochemical elements with an improved level of reproducibility of the predetermined diffusion resistance of their thin flat space, which assures consistent operating characteristics and quality.

BRIEF DESCRIPTION OF THE DRAWINGS

The above and optional objects, features and advantages of the present invention will become more apparent by reading the following description of preferred embodiments of the invention, when taken in conjunction with the accompanying drawings, in which.

DESCRIPTION OF THE PREFERRED EMBODIMENTS

Figure 1:
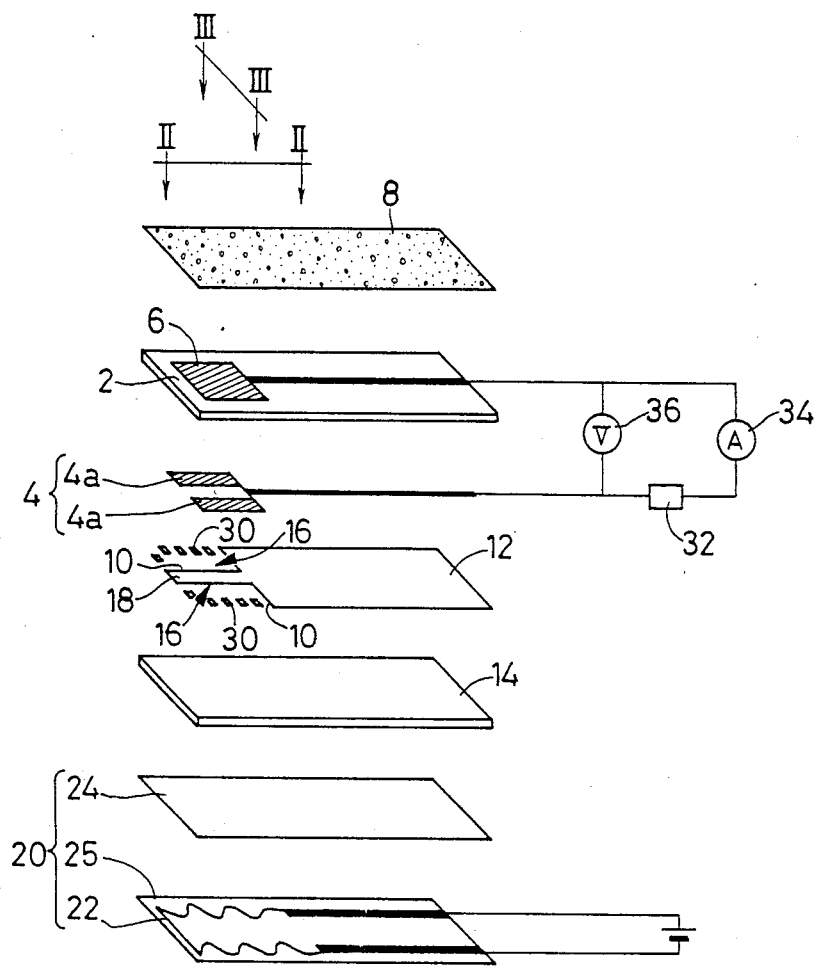
FIG. 1 is an exploded view in perspective of one embodiment of an electrochemical element of the invention of an electrochemical device in the form of an oxygen sensor.

To further clarify the principle of the present invention, the preferred arrangements of an electrochemical element suitable for implementation of the invention will now be described in detail by reference to the accompanying drawings.

Referring first to FIGS. 1-4, there is shown a basic arrangement of an electrochemical element in the form of an oxygen sensor suitably used for controlling the combustion of an air-fuel mixture in an engine of a motor vehicle. Reference numeral 2 designates a substrate formed of a solid electrolyte such as zirconia ceramics containing yttria. On the opposite major surfaces of the substrate 2, there are disposed a pair of electrodes, respectively, i.e., a first electrode 4 consisting of two electrically connected portions 4a, 4a, and a second electrode 6. These solid electrolyte substrate 2, and the pair of electrodes 4, 6 integral with the substrate 2 constitute an electrochemical cell. On one side of the electrochemical cell on which the second electrode 6 is disposed, there is disposed a porous ceramic layer 8 made of alumina or the like, so that the ceramic layer 8 protects the second electrode 6 from direct exposed to a gas to be measured (hereinafter referred to as "measurement gas" if appropriate). On the other side of the cell on which the first electrode 4 is disposed, there are provided a spacer layer 12 and a planar covering member 14 that are superposed on each other. The spacer layer 12 has a pair of rectangular cutouts 10, 10 formed in transversely opposite portions at its one longitudinal end, such that the two cutouts 10, 10 to define a transversely central extension 18 which extends along the length of the spacer layer 12. The spacer member 12 is sandwiched by the solid electrolyte substrate 2 of the upper electrochemical cell, and the lower covering member 14, so that the substrate 12 and the covering member 14 cooperate with the two rectangular cutouts 10, 10 to define a pair of rectangular thin flat spaces 16, 16 which have a predetermined diffusion resistance to the measurement gas.

Figure 4:
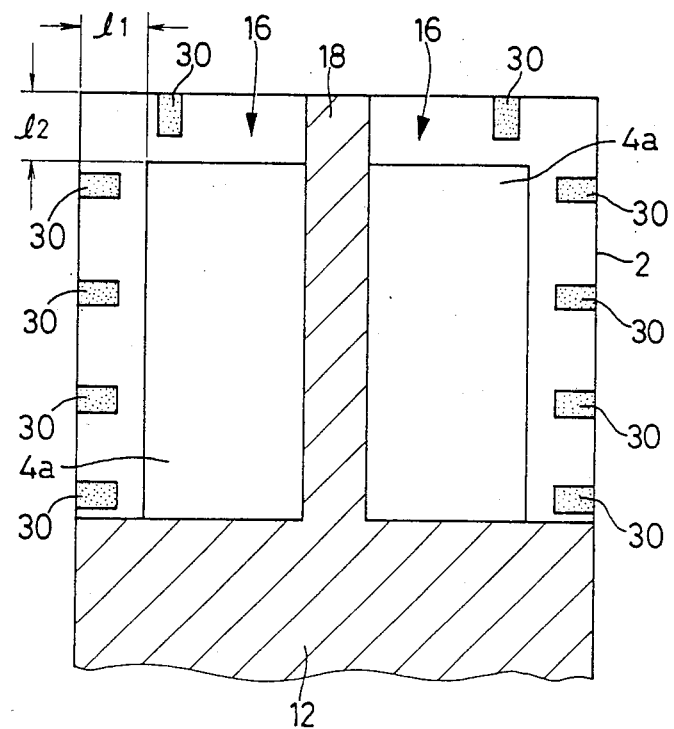
FIG. 4 is a fragmentary cross sectional view taken alone line IV—IV of FIG. 3(a)

Described more particularly, the two thin flat spaces 16, 16 are formed on the opposite sides of the central extension 18 of the spacer layer 12, in symmetric relation with each other with respect to the central extension 18 in the direction of width of the spacer layer 12. The thin flat spaces 16, 16 thus formed within the electrochemical element are open in the appropriate end face and the opposite side faces of the element, so that the spaces 16, 16 communicate, via the inlet openings in these end and side faces, with the external space in which the measurement gas exists. In this arrangement, therefore, the measurement gas is introduced into the thin flat spaces 16, 16 through their inlet openings, under the predetermined diffusion resistance. The two portions 4a, 4a of the first electrode 4 are located such that their edges are spaced from the appropriate open ends or inlets of the thin flat spaces 16, 16, by predetermined suitable distances 11 and 12, as indicated in FIG. 4. The first electrode portions 4a, 4a, which are thus disposed in the inner portions of the thin flat spaces 16, 16, are exposed to the introduced measurement gas.

On the outer side of the planar covering member 14, there is formed a heater 20 which is activated to keep the electrochemical cell at a suitable operating temperature, even while the temperature of the measurement gas is low. The heater 20 includes a heat generating element 22, and two electrically insulating layers 24, 25 which support the heat generating element 22 so as to sandwich the same. For increased structural integration of the present laminar electrochemical element, the spacer layer 12 and the covering member 14 are preferably made of zirconia ceramics or other solid electrolyte material similar to the solid electrolyte material of the substrate 2. However, the spacer layer 12 and the covering member 14 may be formed of a material different from that of the solid electrolyte substrate 2.

Figure 2A:
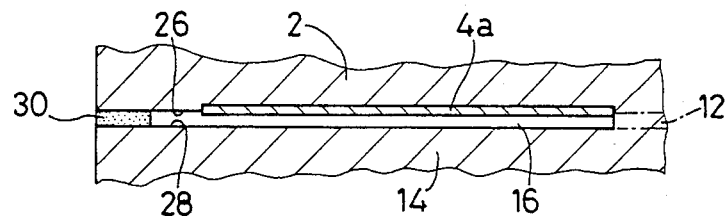
FIG. 2(a) and FIG. 3(a) are fragmentary enlarged views in cross section taken alone line II—II and line III—III of FIG. 1, respectively.
Figure 2B:
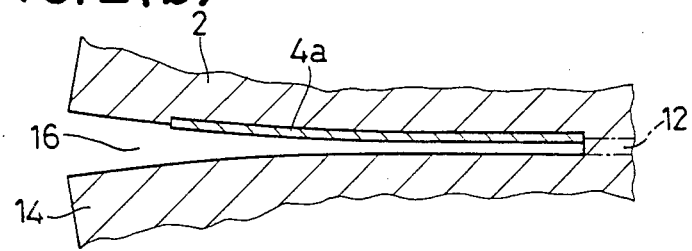
FIGS. 2(b) and FIG. 3(b) are fragmentary enlarged cross sectional views corresponding to FIGS. 2(a) and 3(a), respectively, showing a conventional electrochemical element.
Figure 3A:
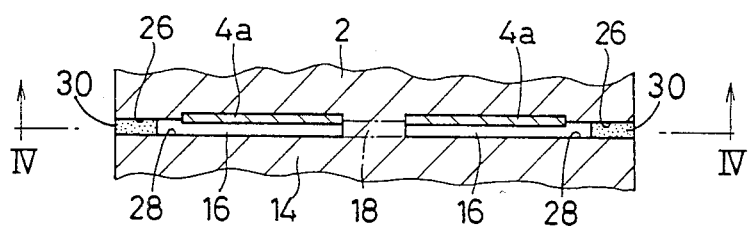
Figure 3B:
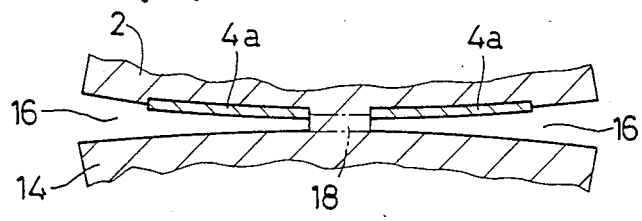

As indicated in FIGS. 2(a) and 3(a), the thickness of the thin flat spaces 16, 16 formed within the electrochemical element is determined by the surface 26 of the substrate 2 on which the first electrode 4 (its two portions 4a, 4a) is disposed, and the surface 28 of the covering member 14 opposed to the surface 26. As shown in FIGS. 1, 2(a), 3(a) and 4, a plurality of ceramic bridging members 30 are disposed, in spaced-apart relation with each other, within the thin flat spaces 16, 16, more specifically, in the portions of the spaces 16, 16 adjacent to their inlet openings, so that the bridging members 30 connect the two opposed flat surfaces 26, 28, so as to bridge a gap between the two opposed flat surfaces 26, 28. In other words, the thickness of the thin flat spaces 16, 16, particularly of their portions adjacent to their open ends, is determined by the thickness of the bridging members 30, which hold the two opposed flat surfaces 26, 28 of the substrate 2 and the covering member 14 apart from each other, in order to maintain the predetermined diffusion resistance of the thin flat spaces 16, 16 defined by the opposed surfaces 26, 28. Namely, the bridging members 30 contribute to maintain the resistance of diffusion of the measurement gas through the thin flat spaces 16, 16 from their inlets toward the inwardly located portions 4a, 4a of the first electrode 4.

If, on the contrary, the bridging members 30 were not provided between the two opposed flat surfaces 26, 28 as in the present embodiment, the substrate 2 and the covering member 14 defining the thin flat spaces 16, 16 would warp or deflect or otherwise be deformed in the process of their firing, whereby the inlet portions of the thin flat spaces 16, 16 are excessively widened or narrowed. Thus, in the absence of the bridging members 30, it would be extremely difficult to form the thin flat spaces 16, 16 with a predetermined thickness, or to provide the spaces 16, 16 with a suitable diffusion resistance. In other words, conventional electrochemical elements which do not incorporate the bridging members 30 tend to have a undesirable variation in the diffusion resistance from one element to another.

The electrochemical element thus constructed according to the invention is connected to an external DC power source 32, as is well known in the art, to apply an electric current between the first and second electrodes 4, 6 of the electrochemical cell, so that ions of a component of the measurement gas are moved from the first electrode 4 to the second electrode 6, or from the second electrode 6 to the first electrode 4. The concentration of the component whose ions diffuse toward the first electrode 4, or the concentration of a component which causes reaction of the above-indicated component, is detected by using an ammeter 34 and a voltmeter 36, according to a commonly known method.

The electrochemical element is manufactured with various methods as appropriate, such as green sheet lamination, printing with pastes, or bonding. In the manufacture, the selected material for the bridging members 30 is applied by screen printing or other suitable method, so that the bridging members 30 are formed so as to bridge a gap between the surface 26 of the solid electrolyte substrate 2, and the opposite surface 28 of the covering member 14, by co-firing the individual members of the element.

The solid electrolyte substrate 2 of the electrochemical cell of the element may be made of $SrCe_{0.95}Yb_{0.05}O_{3-\alpha}$, and other proton conductive materials, or $CaF_2$ or other halogen-ion conductive materials, as well as zirconia ceramics, solid solutions of $Bi_2O_3$—$Y_2O_3$ or other oxygen-ion conductive materials. The electrodes 4, 6 are made of metals such as platinum, rhodium, palladium, gold or nickel, or electrically conductive compounds such as stannic oxide. These materials are used with a ceramic powder, and applied in the form of a slurry or paste, by coating, printing or spraying. The applied materials are baked to create cermet electrodes. Other methods such as plating, sputtering, CVD, thermal decomposition of an aqueous solution, may be used to form the electrodes 4, 6.

Figure 5:
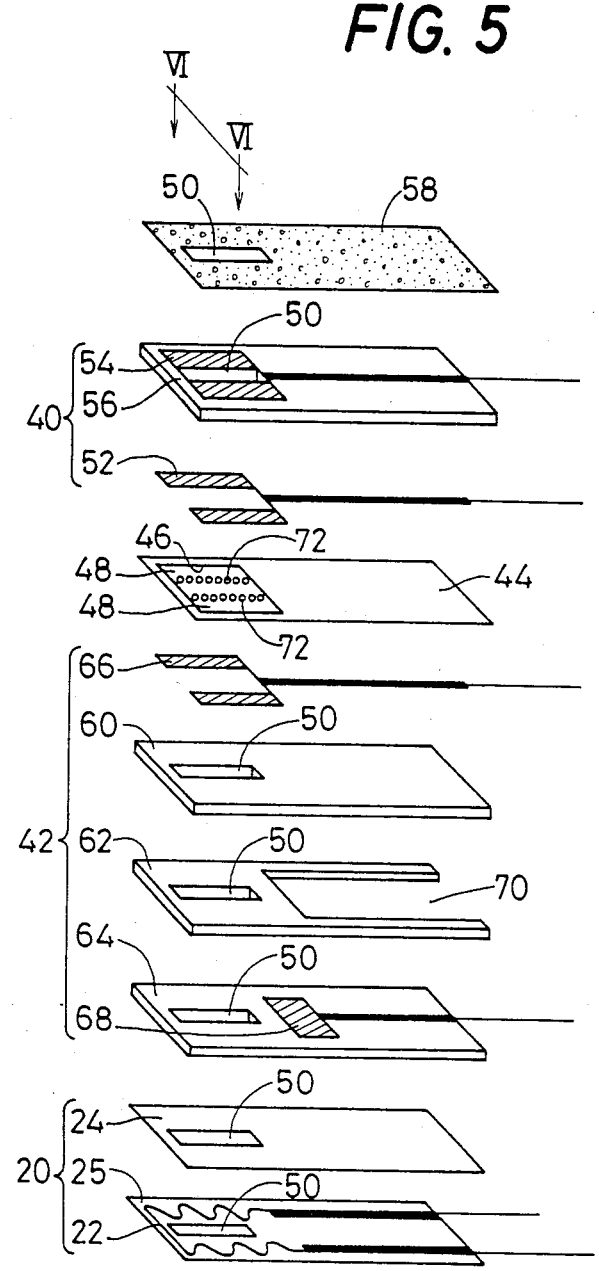
FIG. 5 is an exploded perspective view corresponding to FIG. 1, showing another embodiment of the electrochemical element of the invention.
Figure 6:
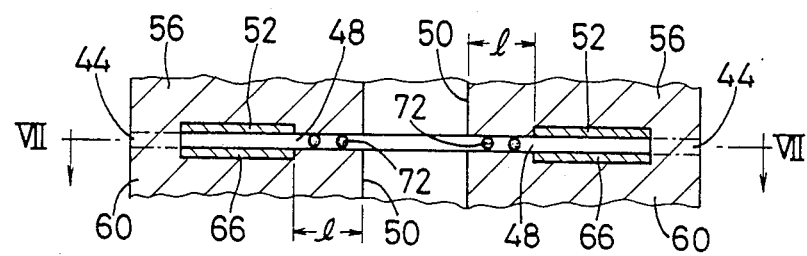
FIG. 6 is a fragmentary enlarged view in cross section taken along line VI—VI of FIG. 5.
Figure 7:
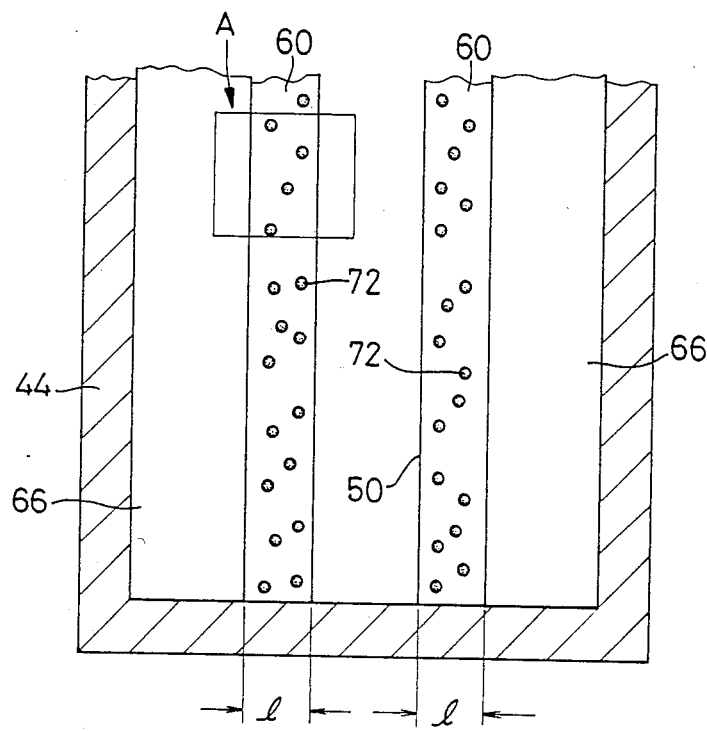
FIG. 7 is a cross sectional view taken along line VII—VII of FIG. 6.

Referring next to FIGS. 5–7, there is shown another embodiment of an electrochemical element of the invention having an arrangement different from that of the preceding embodiment. The present electrochemical element includes two electrochemical cells, that is, an electrochemical pumping cell 40 and an electrochemical sensing cell 42, and further includes a heater 20. Between the two electrochemical cells 40, 42, there is formed a spacer layer 44 which has a square cutout 46 to provide thin flat spaces 48 (as most clearly shown in FIG. 6).

Described in greater detail, the present electrochemical element has a gas inlet aperture 50 formed through the various layers of the element in the direction of lamination. The electrochemical pumping cell 40 includes an inner pumping electrode 52 and an outer pumping electrode 54, and a solid electrolyte substrate 56 having the opposite major surfaces on which the inner and outer pumping electrodes 52, 54 are disposed, respectively. Each electrode 52, 54 consists of two electrically connected portions which are located on the opposite sides of the gas inlet aperture 50. As in the preceding embodiment, a porous ceramic layer 58 is disposed so as to cover the outer pumping electrode 54 of the electrochemical pumping cell 40.

The electromechanical sensing cell 42 includes planar passage-defining members 60, 62 and 64 made of a solid electrolyte, a measuring electrode 66 disposed on the passage-defining member 60 adjacent to the pumping cell 40, a reference electrode 68 disposed on the passage-defining member 64 adjacent to the heater 20. The measuring electrode 66 consists of two portions which are located on the opposite sides of the gas inlet aperture 50, and are exposed to the measurement gas in the thin flat spaces 48, 48. The reference electrode 68 is exposed to a reference gas in a reference gas passage 70 defined by the three passage-defining members 60, 62 and 64. The reference gas passage 70 is open to the atmosphere at one longitudinal end of the electrochemical element, so that the ambient air is used as the reference gas.

In the electrochemical element thus constructed, the thin flat spaces 48, 48 are formed in the square cutout 46 in the spacer layer 44, between the electrochemical pumping and sensing cells 40, 42. The two electrically connected portions of the inner pumping electrode 52 and the measuring electrode 66 are disposed so that each electrode portion is spaced a predetermined distance l away from the gas inlet aperture 50. In the areas of the thin flat spaces 48, 49 adjacent to the gas inlet aperture 50, that is, in the areas of the flat spaces 48, 48 corresponding to the predetermined distance l, there are formed a suitable number of ceramic bridging members in the form of solid electrolyte grains or particles 72 having a diameter which is equal to or slightly larger than the thickness of the thin flat spaces 48, 48. The grains 72 are substantially mutually spaced apart from each other, as most clearly shown in FIG. 7. Further, the ceramic grains 72 are located away from the inlet of the thin flat spaces 48, 48 which communicate with the inlet aperture 50 as shown in FIG. 6. Each solid electrolyte grain 72 bridges a gap between the opposed surfaces of the solid electrolyte substrate 56 and the upper passage-defining member 60, which opposed surfaces cooperate with the cutout 46 to define the thin flat spaces 48, 48. Thus, the solid electrolyte grains or ceramic bridging member 72 serve to determine the thickness of the thin flat spaces 48, 48, particularly at their inlet areas adjacent to the gas inlet aperture 50. Namely, the ceramic grains or particles 72 bridging the upper and lower solid electrolyte members 56, 60 effectively prevent a change in the thickness of the thin flat spaces 48, 48, due to deformation of the solid electrolyte members 56, 60 during firing thereof. Thus, the ceramic grains 72 are effective to maintain a desired thickness of the thin flat spaces 48, 48.

According to the electrochemical element described above, an external measurement gas is introduced into the thin flat spaces 48, 48 through the gas inlet aperture 50 formed through the element. The measurement gas which has reached the inlets of the thin flat spaces 48, 48 diffuses toward the inner pumping electrode 52 and the measuring electrode 66 which are disposed the predetermined distance l away from their inlets (gas inlet aperture 50). In this way, the electrodes 52, 66 are exposed to the measurement gas which has diffused through the thin flat spaces 48, 48. Since the predetermined thickness of the thin flat spaces 48, 48 is maintained by the ceramic bridging grains 72, the predetermined suitable resistance of diffusion of the measurement gas through the thin flat spaces 48, 48 is maintained. Accordingly, the ceramic bridging grains 72 contribute to minimizing a variation in the measured values of the measurement gas from one element to another.

In determining the concentration of a component of the measurement gas by the electrochemical element constructed as described above, a DC current is applied between the pumping electrodes 52, 54, to effect a well-known pumping operation in which oxygen ions (component to be measured) are moved through the solid electrolyte substrate 56, so that the oxygen concentration of the measurement gas within the thin flat spaces 48, 48 is controlled by the pumping action. In the meantime, an electromotive force is induced between the measuring electrode 66 of the sensing cell 42 which is exposed to the controlled atmosphere in the thin flat spaces 48, 48, and the reference electrode 68 exposed to the reference gas in the reference gas passage 70. The induced electromotive force is measured by an external voltmeter to which the electrodes 66, 68 are connected through their leads. The concentration of the specific component (oxygen) of the measurement gas introduced in the thin flat spaces 48, 48 is detected based on the pumping current flowing through the electrochemical pumping cell 40, and the electromotive force induced in the electrochemical sensing cell 42.

Figure 8:
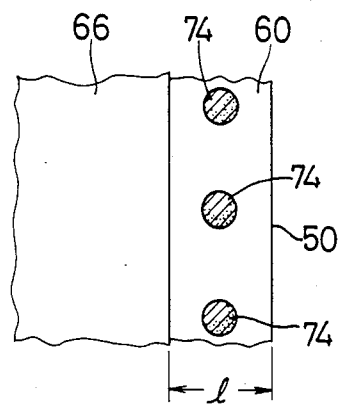
FIGS. 8 and 9 are fragmentary enlarged views corresponding to a portion A indicated in FIG. 7, illustrating different forms of ceramic bridging members used in further embodiments of the invention.
Figure 9:
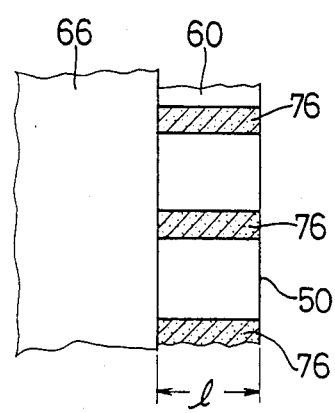

FIGS. 8 and 9 illustrate modified forms of ceramic bridging means which may be used in place of the ceramic grains or particles 72. The bridging means shown in FIG. 8 consists of a plurality of ceramic disks 74 which are disposed in spaced-apart relation with each other, in the areas of the thin flat spaces 48, 48 corresponding to a predetermined distance l between the gas inlet aperture 50 and the corresponding edge of the electrode 66. The array of the ceramic disks 74 is located away from the inlet aperture 50 (in the right direction in FIG. 8), and bridges a gap between the solid electrolyte substrate 56 and the upper passage-defining member 60. The bridging means shown in FIG. 9 consists of a plurality of ceramic strips 76 which are spaced apart from each other in the direction of length of the electrode 66. These ceramic means in the form of the ceramic disks 74 and the ceramic strips 76 are also effective to protecting the thin flat spaces 48, 48 against deformation, and therefore contribute to maintaining the predetermined diffusion resistance of the thin flat spaces 48, 48.

Figure 10:
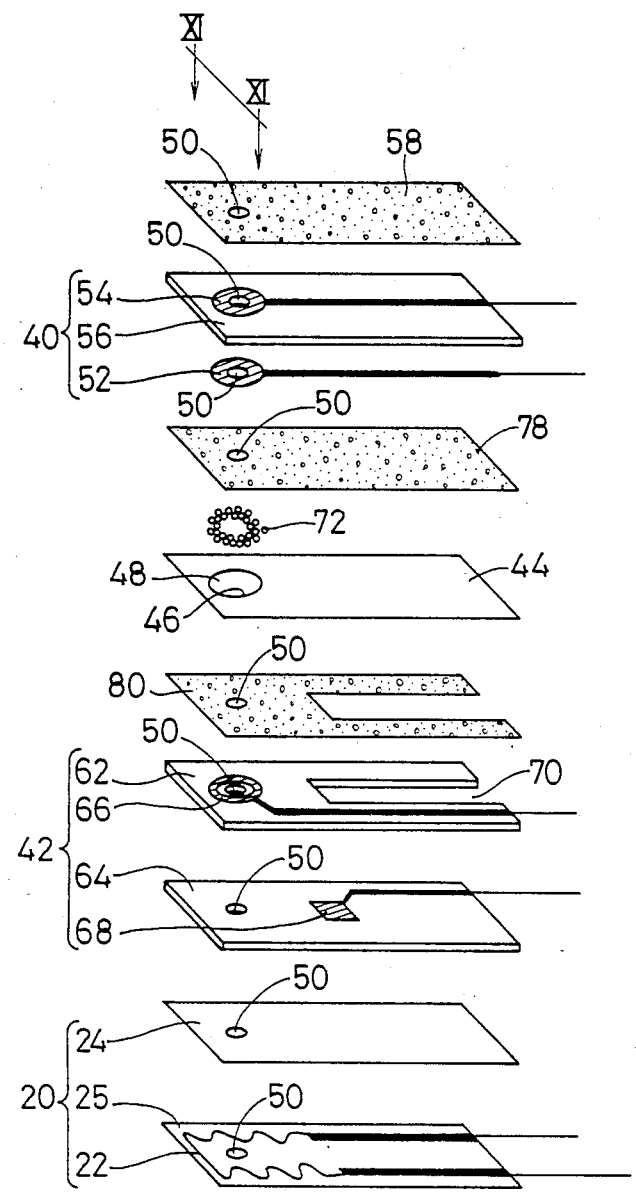
FIG. 10 is an exploded perspective view corresponding to FIG. 1, depicting a still further embodiment of the invention.
Figure 11:
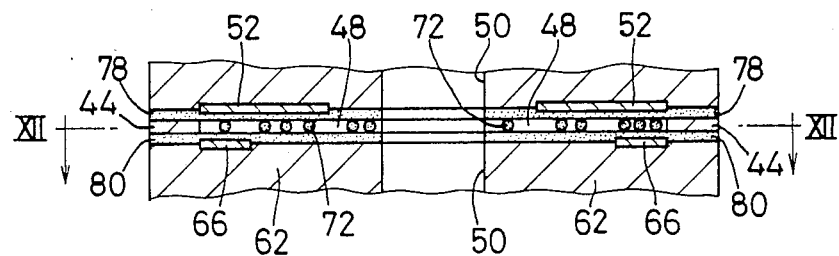
FIG. 11 is a fragmentary enlarged view in cross section taken along line XI—XI of FIG. 10.
Figure 12:
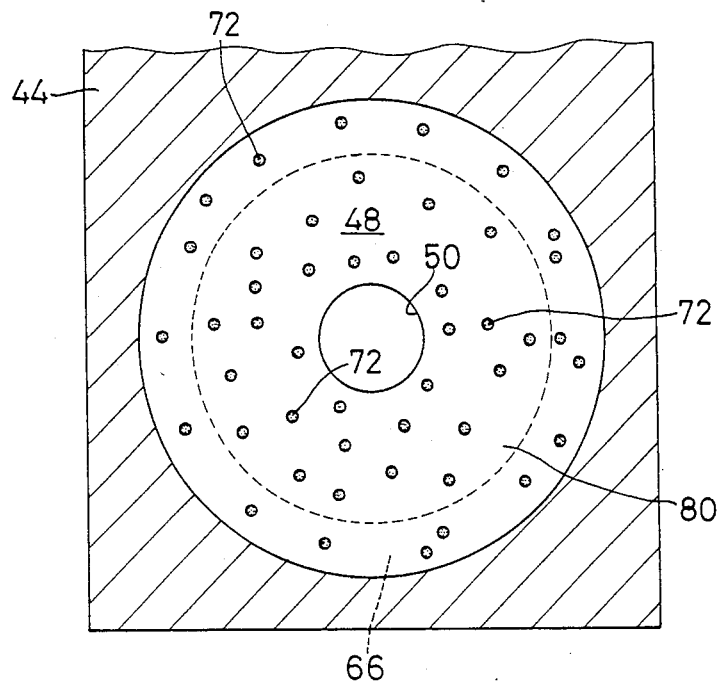
FIG. 12 is a fragmentary view in cross section taken along line XII—XII of FIG. 11.

Referring further to FIGS. 10–12, there is shown a further modified embodiment of an electrochemical element of the present invention, which includes the electrochemical pumping and sensing cells 40, 42 and the heater 20, like the preceding embodiment of FIG. 5. The thin flat space 48 is provided in a circular cutout 46 formed in the spacer layer 44 between the pumping and sensing cells 40, 42. However, the present embodiment is different from the preceding embodiment in that porous ceramic layers 78, 80 made of alumina or similar materials are provided for protecting the inner pumping electrode 52 of the pumping cell 40, and the measuring electrode 66 of the sensing cell 42. In this arrangement, the inner pumping electrode 52 is substantially exposed through the porous ceramic layer 78 to the atmosphere in the thin flat spaces 48, while the measuring electrode 66 is substantially exposed to the same atmosphere through the porous ceramic layer 80. In the instant electrochemical element, the gas inlet aperture 50 is circular in cross section, and the inner and outer pumping electrodes 52, 54 of the pumping cell 40, and the measuring electrode 54 of the sensing cell 40 are ring-shaped.

Over the entire area of the circular or annular thin flat space 48 formed between the porous ceramic layer 78 protecting the inner pumping electrode 52 and the porous ceramic layer 80 protecting the measuring electrode 66, a multiplicity of ceramic grains or particles 72 are disposed so as to bridge a gap between the two porous ceramic layers 78, 80, thereby determining the thickness of the thin flat space 48 which communicates with the external measurement-gas space through the gas inlet aperture 50. Namely, the ceramic grains 72 contact the opposite surfaces of the porous ceramic layers 78 and 80. Thus, the ceramic grains 72 act to maintain the predetermined diffusion resistance of the thin flat space 48. As seen in FIG. 12, even the radially innermost grains 72 are located away from central inlet aperture 50.

The measurement gas introduced through the gas inlet aperture 50 diffuses between the scattered ceramic grains 72 in the radially outward direction of the annular thin flat space 48, toward the inner pumping electrode 52 and the measuring electrode 66, under the predetermined diffusion resistance. For increased firing integration and adherence of the ceramic bridging grains 72 to the porous ceramic layers 78, 80, the ceramic grains 72 may be advantageously made of the same ceramic material as the porous ceramic layers 78, 80. The ceramic grains 72 which bridge the two porous ceramic layers 78, 80 effectively protect the thin flat space 48 from deformation during firing of the element. Preferably, the ceramic grains 72 have a diameter which is equal to or slightly larger than the desired thickness of the thin flat space 48.

Figure 13:
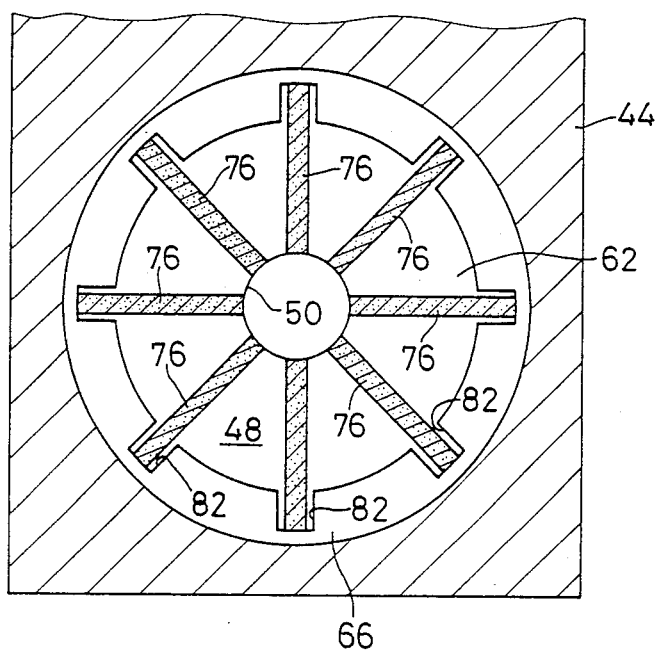
FIG. 13 is a view corresponding to FIG. 12, showing a further modified form of the ceramic bridging member used in a yet further embodiment of the invention.

FIG. 13 shows another form of ceramic bridging means in the form of radial ceramic strips 76 which are disposed in the annular thin flat space 48 (similar to the space 48 of the preceding embodiment), so as to extend radially from the circular gas inlet aperture 50. The radial ceramic strips 76 are equi-angularly spaced from each other. The radial ceramic strips 76 extend as far as the measuring electrode 66 located at the radially outermost portion of the thin flat space 48. The measuring electrodes 66 has a plurality of cutouts 82 which are adapted to accommodate the outward ends of the corresponding radial ceramic strips 76, in order to prevent the outward ends of the strips 76 from lying on the electrode 66. While the radial ceramic strips 76 of the present embodiment extend from the periphery of the circular aperture 50, the inward ends of the strips 76 may be positioned a suitable distance away from the periphery of the aperture 50.

As described above, the present invention provides an electrochemical element wherein the thickness of the thin flat space or spaces (16, 48) is determined by suitable ceramic bridging means such as the ceramic bridging members or strips 30, 76, ceramic grains or particles 72, and ceramic disks 74, which are formed so as to bridge a gap between two opposed flat surfaces which define the thickness of the thin flat space or spaces. It is considered possible to replace such ceramic bridging means by a porous layer which fills a suitable thin flat cavity formed in the element and which has a predetermined diffusion resistance to the measurement gas.

However, the proposed diffusion-resistant porous layer accommodated in a thin flat cavity creates another problem that the measurement gas will not be sufficiently supplied to the portions of the solid electrolyte of a cell which contact the porous layer, more particularly, the portions of the solid electrolyte which contact the electrodes located in the area of the flat cavity remote from its inlet. The insufficient supply of the measurement gas will cause deterioration of the solid electrolyte due to electrolysis at the above-indicated portions. Further, the diffusion-resistant porous layer tends to have uneven distribution of concentration of a measurement component of the measurement gas, which results in lowering the measuring accuracy of the electrochemical element.

The use of ceramic bridging members within a thin flat space or spaces according to the principle of the invention does not have a problem as encountered in the above case wherein a thin flat cavity is filled with a diffusion-resistant porous layer. Namely, the ceramic bridging members provided according to the invention does not fill the thin flat space or spaces, but permit a sufficient volume of spaces to be left between the bridging members, whereby the measurement gas adjacent to the electrodes will not have a difference in the concentration of the measurement component. In the arrangement of FIG. 13 wherein the cutouts 82 prevent the electrode 66 from contacting the ceramic strips 76, insufficient supply of the measurement gas to the solid electrolyte member 62 due to the presence of the ceramic strips 76 will not cause electrolysis deterioration of the portions of the solid electrolyte member 62 which correspond to the cutouts 82. Further, in the case where ceramic bridging members in the form of the ceramic grains 72 are used as illustrated in FIGS. 10–12, the supply of the measurement gas to the solid electrolyte will not be substantially restricted by the ceramic grains 72, since the size of the ceramic grains 72 is as small as the thickness of the thin flat space 48. Furthermore, the porous protective ceramic layers 78, 80 covering the electrodes 52, 66 permit flows of the measurement gas past the ceramic bridging members (72) to the portions of the solid electrolyte corresponding to the ceramic bridging members, thereby protecting those portions of the solid electrolyte from electrolysis deterioration.

In the fabrication of the electrochemical elements according to the invention, the electrodes and their leads, spacer layer, porous protective ceramic layers, etc. are screen-printed on the green sheet on the solid electrolyte substrate member of the appropriate cell, so as to obtain a green laminar structure of the cell. This green structure, and other green laminar structures for another cell and the heater are superposed on each other. Thus, the green laminar structure of an electrochemical element is prepared. The prepared green structure is then subjected to a well-known firing process.

To adequately form the thin flat space or spaces previously described, the voids corresponding to the thin flat spaces are filled with a suitable disappearing material as needed, during formation of the laminar green structure of the element. For example, the voids are filled with carbon, paper, sublimable substances, or thermo-setting resins, which will disappear upon firing of the green laminar structure of the element, thereby permitting the intended thin flat spaces to be formed within the fired element. In place of this disappearing filler material, or in addition to this material, a ceramic paste for the ceramic bridging members is applied in the process of preparing the laminar green structure, so that the intended ceramic bridging members are formed within the thin flat space or spaces, upon firing of the green structure, so as to bridge the opposed two flat surfaces which define the thickness of the thin flat space or spaces.

In the case where the ceramic bridging members are provided in the form of the ceramic grains 72 as used in the embodiments of FIGS. 5–7 and FIGS. 10–12, it is preferred to prepare a screen-printing paste which is a mixture consisting of the disappearing material (filler) and the material for the ceramic grains 72. The thus prepared paste is screen-printed in the form of a layer which occupies at least a portion of the void corresponding to the thin flat space. The entire volume of the void may be filled with this layer of the printing paste, or a portion of the volume is filled by the printing paste while the remaining portion is filled with the filler material indicated above. Upon firing the printing paste, the filler material contained therein will disappear, thus contributing to formation of at least a part of the thin flat space. At the same time, the ceramic material contained in the paste is fired into the ceramic grains 72 which connect the two opposed flat surfaces of the thin flat space to each other, and substantially determine the thickness of the thin flat space over its entire area from the inlet to the extremities remote from the inlet.

It is desirable that the ceramic material for the ceramic grains is fired into the ceramic grains (72) at a firing temperature lower than firing temperature of the ceramic materials of the two members (56, 60; 78, 80) which provide the two opposed flat surfaces which define the thin flat spaces 48. The size (diameter) of the ceramic grains (72) must be substantially equal to (equal to or slightly larger than) the desired thickness of the thin flat spaces to be formed.

While the several preferred embodiments of the electrochemical element of this invention have been described, it is to be understood that the invention is not limited thereto, but may be embodied with various changes, modifications and improvements which may occur to those skilled in the art in the light of the foregoing teachings, without departing from the spirit and scope of the invention.

Although the electrochemical element of the invention is advantageously used to detect lean-burned and rich-burned exhaust gases which are produced by an engine of a motor vehicle, as a result of combustion of fuel-lean and fuel-rich air-fuel mixtures, the same element may be equally used as a sensor for detecting exhaust gases emitted as a result of combustion of an air-fuel mixture having the stoichiometric air-fuel ratio, or as other sensors, detectors or controllers adapted to detect nitrogen, carbon dioxide, hydrogen and other components of a fluid which are associated with electrode reaction. Further, the present invention may be embodied as a humidity sensor using a proton-conductive material.

A few examples are given below to illustrate the preferred methods of manufacturing the electrochemical elements according to the invention. It is to be understood that these examples are provided for illustrative purpose only, and that the invention is by no means confined to the precise details of the examples.

EXAMPLE 1

To produce the electrochemical element of FIGS. 10–12, 100 parts by weight of powder mixture consisting of 97 mole % of $ZrO_2$ 'and 3 mole % of $Y_2 \cdot O_3$ 'was mixed with 1 part by weight of clay, 10 parts by weight of polyvinyl butyral, 5 parts by weight of dioctyl phthalate, and 100 parts by weight of trichloroethylene as a solvent. The mixture was prepared as a slurry. The slurry was cast in a known doctor-blading process, to form three green sheets of solid electrolyte of 0.6 mm thickness to give the solid electrolyte substrate 56 and the passage-defining members 62, 64 which are shown in FIG. 10.

On the appropriate surfaces of the three solid electrolyte green sheets, unfired layers for the electrodes 52, 54, 66, 68 were screen-printed as indicated in FIG. 10, by using a paste which was prepared by adding 8% by weight of polyvinyl butyral and 40% by weight of butyl carbitol, to a powder mixture which consists of 90% by weight of platinum and 10% by weight of $ZrO_2$.

Further, a paste for forming unfired layers of the porous ceramic layers 58, 28, 80, and the insulating layer 24 was prepared by adding 10% by weight of polyvinyl butyral, 5% by weight of dibutyl sebacate and 40% by weight of butyl carbitol, to a powder mixture consisting of 98% by weight of $Al_2O_3$, 1.5% by weight of $SiO_2$ and 0.5% by weight of CaO. The prepared paste was applied by screen-printing to the appropriate solid electrolyte green sheets.

A paste for the heat generating element 22 was prepared by adding 8% by weight of ethyl cellulose and 40% by weight of butyl carbitol, to a powder mixture of 80% b weight of platinum and 20% by weight of $Al_2O_3$. With the prepared paste, the heat generating element 22 was screen-printed on the unfired layer of the insulating layer 24. Further, an unfired layer of the insulating ceramic layer 25 was screen-printed so as to cover the heat generating element 22, by using a paste which was prepared from a powder mixture of 79 mole % of $ZrOhd\ 2$, 11 mole % of $Nb_2O_5$ and 10 mole % of $Y_2O_3$, mixed with 80% by weight of polyvinyl butyral, 3% by weight of dibutyl sebacate and 40% by weight of butyl carbitol. With the same paste, an unfired layer of the spacer layer 44 was screen-printed on the unfired layer of the porous ceramic layer 80, as indicated in FIG. 10.

Subsequently, a paste for forming the ceramic grains 72 (ceramic bridging means) as indicated in FIG. 12 was prepared by adding 12% by weight of polyvinyl butyral, 3% by weight of dibutyl sebacate and 40% by weight of butyl carbitol, to 30% by weight of $Al_2O_3$-$SiO_2$-CaO powder mixture (98wt. % of $Al_2O_3$, 1.5 wt. % of $SiO_2$ and 0.5 wt. % of CaO) of a grain size ranging from 8 microns to 12 microns, and 70% by weight of carbon powder. This paste was applied by screen-printing, so as to fill the circular cutout 46 in the unfired spacer layer 44 on the unfired porous ceramic layer 80.

The three green sheets for the solid electrolyte members 56, 62 and 64, with the various unfired layers screen-printed thereon as described above, were superposed on each other, as indicated in FIG. 10. The obtained unfired laminar green structure was then heated and pressed, to obtain one chip laminar structure. This unfired structure was finally fired at 1400° C. As a result, the oxygen sensor (electrochemical element) of FIG. 12 having the ceramic grains 72 in the thin flat space 48 was obtained.

In this manner, a total of ten oxygen sensors were prepared. For each sensor, a DC power source was connected between the pumping electrodes 52, 54, a voltmeter connected between the measuring and reference electrodes 66, 68, and a DC power source connected to the heat generating element 22. With 12 V applied to the heat generating element 22 to hold the sensor at a suitable operating temperature, the sensor was operated in the atmosphere. For all of the ten oxygensensors, the electric current flowing through the pumping cell 40 was measured at the moment the electromotive force induced in the sensing cell 42 was 0.2 V.

The measurements of the pumping current were 12 mA plus or minus 1 mA. This indicates a considerably reduced variation in the measurement, as compared with the measurements of 14 mA plus or minus 6 mA on the conventional sensors which do not have the ceramic bridging means 72. Thus, the ceramic bridging means 72 provided according to the invention demonstrated excellent effects on the measuring accuracy of the sensors.

EXAMPLE 2

To produce the electrochemical element of FIGS. 5–7, four green sheets for the solid electrolyte members 56, 60, 62 and 64 were prepared from the same solid electrolyte as used in Example 1.

On the three green sheets for the solid electrolyte members 56, 62 and 64, unfired layers of the electrodes 52, 54, 66 and 68 were screen-printed as indicated in FIG. 5, with the same paste as used for the electrodes in Example 1. On the surface of the unfired electrode 54 on the solid electrolyte green sheet 56 and on the surface of the solid electrolyte green sheet 64 opposite to the unfired electrodes 68, unfired layers of the porous ceramic layer 58 and the insulating layer 24 were screen-printed with the same paste as used for the corresponding layers in Example 1. Further, the same paste as used for the heat generating element 22, ceramic layer 25 and spacer layer 44 in Example 1 was applied to the unfired insulating layer 24 and the solid electrolyte green sheet 60, in order to form the corresponding parts, as shown in FIG. 5.

Then, a paste for forming the ceramic grains 72 as shown in FIG. 7 was prepared by adding 15% by weight of polyvinyl butyral, 7% by weight of dibutyl sebacate and 40% by weight of butyl carbitol, to a mixture which consists of 5% by weight of a powder mixture of 8–12 micron grain size consisting of 100 parts by weight of $ZrO_2$—$Y_2O_3$ (97 mole % of $ZrO_2$ and 3 mole % of $Y_2O_3$) and 3 parts by weight of clay, and 95% by weight of bakelite powder of 3 micron grain size. The prepared paste was applied by screen-printing to the surface of the solid electrolyte green sheet 60, in the form of strips extending in parallel on the opposite sides of the gas inlet aperture 50, as shown in FIG. 7.

The four green sheets for the solid electrolyte members 56, 60, 62 and 64, with the various unfired layers screen-printed thereon, were superposed on each other, as indicated in FIG. 5. The obtained unfired laiminar green structure was then heated and pressed, to obtain one chip laminar structure. This unfired structure was finally fired at 1400° C. As a result, the oxygen sensor (electrochemical element) having the two arrays of ceramic grains 72 adjacent to the inlets of the thin flat spaces 48, 48 as shown in FIG. 7 was obtained.

The thus prepared oxygen sensor was cut in the cross sectional plane VI—VI of FIG. 5, and the cross sectional surface of FIG. 6 was observed to check the thin flat spaces 48, 48. The observation revealed that each flat space 48 had a substantially constant thickness over its entire width from the inlet to the extremity remote from the gas inlet aperture. Further, it was found that the ceramic grains 72 were fired integrally with the solid electrolyte substrate 56 and the passage-defining member 60. For comparison, a conventional oxygen sensor without any ceramic bridging members in the thin flat spaces was prepared. The observation of the conventional sensor revealed widening or narrowing of the thin flat spaces at their inlet portions adjacent to the gas inlet aperture.

What is claimed is:
1. An electrochemical element, comprising:
a planar solid electrolyte body;
at least two electrodes including a first electrode and a second electrode which are disposed on said planar solid electrolyte body;
a first means for defining a thin flat space which has a predetermined diffusion resistance to restrict diffusion of a measurement gas to said first electrode, said thin flat space communicating with a measurement-gas space in which said measurement gas exists via a gas inlet aperture, said gas inlet aperture being formed through said electrochemical element in a plane normal to and intersecting a plane of said thin flat space, such that an inlet is formed in said thin flat space at a portion of said gas inlet aperture which intersects said thin flat space, said first electrode being substantially exposed to said measurement gas in said thin flat space, said means for defining a thin flat space including two opposed flat surfaces parallel to said plane of said thin flat space, said first electrode being disposed on a first of said two opposed flat surfaces and contacting a first portion of said first opposed flat surface, such that said first electrode is spaced a predetermined distance away from said inlet of said thin flat space in a direction parallel to said plane of the thin flat space, said measurement gas being introduced through said inlet into said thin flat space; and a second means for substantially defining the thickness of said thin flat space, said second means comprising ceramic bridging means having a thickness of 8-12 microns disposed in said thin flat space, said ceramic bridging means contacting a second portion of said first flat surface and the second surface of said two opposed flat surfaces, thereby bridging a gap between said two opposed flat surfaces, said ceramic bridging means being located away from the intersection of said gas inlet aperture and said thin flat space in said direction, and disposed in an area of said thin flat space corresponding to said predetermined distance, and thereby being in a non-contacting relationship with said first electrode.

2. An electrochemical element according to claim 1, wherein said means for defining a thin flat space and said ceramic bridging means comprise substantially the same material.

3. An electrochemical element according to claim 1, wherein said ceramic bridging means consists of a plurality of mutually spaced-apart ceramic members which are disposed at least in an area of said thin flat space adjacent to an inlet of said thin flat space through which said measurement gas is introduced into said thin flat space.

4. An electrochemical element according to claim 1, wherein said ceramic bridging means consists of a plurality of ceramic grains having a diameter which is substantially equal to the thickness of said thin flat space.

5. An electrochemical element according to claim 1, wherein said planar solid electrolyte body, and said first and second electrodes constitute a first electrochemical cell, and further comprising a second electrochemical cell which includes another planar solid electrolyte body, and another pair of electrodes, said thin flat space being formed between said first and second electrochemical cells.

6. An electrochemical element according to claim 1, further comprising a protective layer disposed between said bridging means and said first electrode, for preventing said bridging means from contacting said surface of said first electrode.

7. An electrochemical element, comprising:
a planar solid electrolyte body;
at least two electrodes including a first electrode and a second electrode which are disposed on said planar solid electrolyte body;
a first means for defining a thin flat space which has a predetermined diffusion resistance to restrict diffusion of a measurement gas to said first electrode, and which communicates with a measurement-gas space in which said measurement gas exists via a gas inlet aperture, said gas inlet aperture being formed through said electrochemical element in a plane normal to and intersecting a plane of said thin flat space, such that an inlet is formed in said thin flat space at a portion of said gas inlet aperture which intersects said thin flat space, said first electrode being spaced a predetermined distance away from said inlet of said thin flat space in a direction parallel to said plane of the thin flat space, said measurement gas being introduced through said inlet into said thin flat space, said first electrode being substantially exposed to said measurement gas in said thin flat space, said means for defining a thin flat space including two opposed flat surfaces parallel to said plane of said thin flat space; and a second means for substantially defining the thickness of said thin flat space, said second means comprising a plurality of ceramic grains having a diameter of 8-12 microns and being substantially equal to a thickness of said thin flat space, and bridging a gap between said two opposed flat surfaces, said ceramic grains being located away from the intersection of said gas inlet aperture and said thin flat space in said direction and disposed in a portion of said thin flat space in a non-contacting relationship with said first and second electrodes, said ceramic grains being substantially mutually spaced apart from each other thereby permitting a flow of said measurement gas through said portion of the thin flat space.

8. An electrochemical element, comprising:
a planar solid electrolyte body;
at least two electrodes including a first electrode and a second electrode which are disposed on said planar solid electrolyte body;
a first means for defining a thin flat space which has a predetermined diffusion resistance to restrict diffusion of a measurement gas to said first electrode, said thin flat space communicating with a measurement gas space in which said measurement gas exists via a gas inlet aperture, said gas inlet aperture being formed through said electrochemical element in a plane normal to and intersecting a plane of said thin flat space, such that an inlet is formed in said thin flat space at a portion of said gas inlet aperture which intersects said thin flat space, said first electrode being exposed to said measurement gas in said thin flat space, said means for defining a thin flat space including two opposed flat surfaces parallel to said plane of said thin flat space, said first electrode being disposed on a first of said two opposed flat surfaces and said second electrode being disposed on the second of said two opposed flat surfaces;
a first protective layer covering said first electrode on said first opposed flat surface;
a second protective layer covering said second electrode on said second opposed flat surface, said first and second protective layers further defining said thin flat space; and a second means for substantially defining the thickness of said thin flat space, said second means comprising ceramic bridging means having a thickness of 8–12 microns disposed in said thin flat space such that said ceramic bridging means is located away from the intersection of said gas inlet aperture and said thin flat space in a direction parallel to said plane of the thin flat space, said ceramic bridging means contacting said first and second protective layers, thereby bridging a gap between said protective layers and substantially determining a thickness of said thin flat space.

9. An electrochemical element, comprising:
a planar solid electrolyte body;
at least two electrodes including a first electrode and a second electrode which are disposed on said planar solid electrolyte body;
a first means for defining a thin flat space which has a predetermined diffusion resistance to restrict diffusion of a measurement gas to said first electrode, said thin flat space communicating with a measurement-gas space in which said measurement gas exists via a gas inlet aperture, said gas inlet aperture being formed through said electrochemical element in a plane normal to and intersecting a plane of said thin flat space, such that an inlet is formed in said thin flat space at a portion of said gas inlet aperture which intersects said thin flat space, said first electrode being substantially exposed to said measurement gas in said thin flat space, said means for defining a thin flat space including two opposed flat surfaces parallel to said plane of said thin flat space, said first electrode being disposed on a first of said two opposed flat surfaces and contacting a first portion of said first opposed flat surface, such that said first electrode is spaced a predetermined distance away from said inlet of said thin flat space in a direction parallel to said plane of the thin flat space, said measurement gas being introduced through said inlet into said thin flat space; and a second means for substantially defining the thickness of said thin flat space, said second means comprising ceramic bridging means disposed in said thin flat space, said ceramic bridging means contacting a second portion of said first flat surface and the second surface of said two opposed flat surfaces, thereby bridging a gap between said two opposed flat surfaces and being in a non-contacting relationship with said first electrode.

10. An electrochemical element according to claim 9, wherein said means for defining a thin flat space and said ceramic bridging means comprise substantially the same material.

11. An electrochemical element according to claim 9, wherein said ceramic bridging means consists of a plurality of mutually spaced-apart ceramic members which are disposed at least in an area of said thin flat space adjacent to an inlet of said thin flat space through which said measurement gas is introduced into said thin flat space.

12. An electrochemical element according to claim 9, wherein said ceramic bridging means consists of a plurality of ceramic grains having a diameter which is substantially equal to the thickness of said thin flat space.

13. An electrochemical element according to claim 9, wherein said planar solid electrolyte body, and said first and second electrodes constitute a first electrochemical cell, and further comprising a second electrochemical cell which includes another planar solid electrolyte body, and another pair of electrodes, said thin flat space being formed between said first and second electrochemical cells.

14. An electrochemical element according to claim 9, further comprising a protective layer disposed between said bridging means and said first electrode, for preventing said bridging means from contacting said surface of said first electrode.

15. An electrochemical element, comprising:
a planar solid electrolyte body;
as least two electrodes including a first electrode and a second electrode which are disposed on said planar solid electrolyte body;
a first means for defining a thin flat space which has a predetermined diffusion resistance to restrict diffusion of a measurement gas to said first electrode, and which communicates with a measurement-gas space in which said measurement gas exists via a gas inlet aperture, said gas inlet aperture being formed through said electrochemical element in a plane normal to and intersecting a plane of said thin flat space, such that an inlet is formed in said thin flat space at a portion of said gas inlet aperture which intersects said thin flat space, said first electrode being spaced a predetermined distance away from said inlet of said thin flat space in a direction parallel to said plane of the thin flat space, said measurement gas being introduced through said inlet into said thin flat space, said first electrode being substantially exposed to said measurement gas in said thin flat space, said means for defining a thin flat space including two opposed flat surfaces parallel to said plane of said thin flat space; and a second means for substantially defining the thickness of said thin flat space, said second means comprising a plurality of ceramic grains having a diameter substantially equal to a thickness of said thin flat space, and bridging a gap between said two opposed flat surfaces, said ceramic grains being disposed in a portion of said thin flat space in a non-contacting relationship with said first and second electrodes, said ceramic grains being substantially mutually spaced apart from each other thereby permitting a flow of said measurement gas through said portion of the thin flat space.

16. An electrochemical element, comprising:
a planar solid electrolyte body;
at least two electrodes including a first electrode and a second electrode which are disposed on said planar solid electrolyte body;
a first means for defining a thin flat space which has a predetermined diffusion resistance to restrict diffusion of a measurement gas to said first electrode, said thin flat space communicating with a measurement gas space in which said measurement gas exists via a gas inlet aperture, said gas inlet aperture being formed through said electrochemical element in a plane normal to and intersecting a plane of said thin flat space, such that an inlet is formed in said thin flat space at a portion of said gas inlet aperture which intersects said thin flat space, said first electrode being exposed to said measurement gas in said thin flat space, said means for defining a thin flat space including two opposed flat surfaces parallel to said plane of said thin flat space, said first electrode being disposed on a first of said two opposed flat surfaces and said second electrode being disposed on the second of said two opposed flat surfaces;

a first protective layer covering said first electrode on said first opposed flat surface;

a second protective layer covering said second electrode on said second opposed flat surface, said first and second protective layers further defining said thin flat space; and a second means for substantially defining the thickness of said thin flat space, said second means comprising ceramic bridging means disposed in said thin flat space, said ceramic bridging means contacting said first and second protective layers, thereby bridging a gap between said protective layers and substantially determining a thickness of said thin flat space.

17. An electrochemical element, comprising:
a planar solid electrolyte body;
at least two electrodes including a first electrode and a second electrode which are disposed on said planar solid electrolyte body;
a first means for defining a thin flat space which has a predetermined diffusion resistance to restrict diffusion of a measurement gas to said first electrode, said thin flat space communicating with a measurement-gas space in which said measurement gas exists, said first electrode being substantially exposed to said measurement gas in said thin flat space, said means for defining a thin flat space including two opposed flat surfaces parallel to a plane of said thin flat space, said first electrode being disposed on a first of said two opposed flat surfaces and contacting a first portion of said first opposed flat surface, such that said first electrode is spaced a predetermined distance away from an inlet of said thin flat space in a direction parallel to said plane of the thin flat space, said measurement gas being introduced through said inlet into said thin flat space; and
a second means for substantially defining the thickness of said thin flat space, said second means comprising ceramic bridging means disposed in said thin flat space, said ceramic bridging means contacting a second portion of said first flat surface and the second surface of said two opposed flat surfaces, thereby bridging a gap between said two opposed flat surfaces, said ceramic bridging means being located away from said inlet of said thin flat space in said direction, and disposed in an area of said thin flat space corresponding to said predetermined distance, and thereby being in a non-contacting relationship with said first electrode.

18. An electrochemical element according to claim 17, wherein said means for defining a thin flat space and said ceramic bridging means comprise substantially the same material.

19. An electrochemical element according to claim 17, wherein said ceramic bridging means consists of a plurality of mutually spaced-apart ceramic members which are disposed at least in an area of said thin flat space adjacent to said inlet of said thin flat space through which said measurement gas is introduced into said thin flat space.

20. An electrochemical element according to claim 17, wherein said ceramic bridging means consists of a plurality of ceramic grains having a diameter which is substantially equal to the thickness of said thin flat space.

21. An electrochemical element according to claim 17, wherein said planar solid electrolyte body, and said first and second electrodes constitute a first electrochemical cell, and further comprising a second electrochemical cell which includes another planar solid electrolyte body, and another pair of electrodes, said thin flat space being formed between said first and second electrochemical cells.

22. An electrochemical element according to claim 17, further comprising a protective layer disposed between said bridging means and said first electrode, for preventing said bridging means from contacting said surface of said first electrode.

23. An electrochemical element, comprising:
a planar solid electrolyte body;
at least two electrodes including a first electrode and a second electrode which are disposed on said planar solid electrolyte body;
a first means for defining a thin flat space which has a predetermined diffusion resistance to restrict diffusion of a measurement gas to said first electrode, and which communicates with a measurement-gas space in which said measurement gas exists, said first electrode being spaced a predetermined distance away from an inlet of said thin flat space in a direction parallel to a plane of said thin flat space, said measurement gas being introduced through said inlet into said thin flat space, said first electrode being substantially exposed to said measurement gas in said thin flat space, said means for defining a thin flat space including two opposed flat surfaces parallel to said plane of said thin flat space; and
a second means for substantially defining the thickness of said thin flat space, said second means comprising a plurality of ceramic grains having a diameter substantially equal to a thickness of said thin flat space, and bridging a gap between said two opposed flat surfaces, said ceramic grains being located away from said inlet of said thin flat space in said direction and disposed in a portion of said thin flat space in a non-contacting relationship with said first and second electrodes, said ceramic grains being substantially mutually spaced apart from each other thereby permitting a flow of measurement gas through said portion of the thin flat space.

24. An electrochemical element, comprising:
a planar solid electrolyte body;
at least two electrodes including a first electrode and a second electrode which are disposed on said planar solid electrolyte body;
a first means for defining a thin flat space which has predetermined diffusion resistance to restrict diffusion of a measurement gas to said first electrode, said thin flat space communicating with a measurement gas space in which said measurement gas exists via a gas inlet aperture, said first electrode being exposed to said measurement gas in said thin flat space, said means for defining a thin flat space including two opposed flat surfaces parallel to said plane of said thin flat space, said first electrode being disposed on a first of said two opposed flat surfaces and said second electrode being disposed on the second of said two opposed flat surfaces;

a first protective layer covering said first electrode on said first opposed flat surface;

a second protective layer covering said second electrode on said second opposed flat surface, said first and second protective layers further defining said thin flat space; and a second means for substantially defining the thickness of said thin flat space, said second means comprising ceramic bridging means disposed in said thin flat space such that said ceramic bridging means is located away from said inlet of said thin flat space in a direction parallel to said plane of the thin flat space, said ceramic bridging means contacting said first and second protective layers, thereby bridging a gap between said protective layers and substantially determining a thickness of said thin flat space.

25. An electrochemical element, comprising:
a planar solid electrolyte body;
at least two electrodes including a first electrode and a second electrode which are disposed on said planar solid electrolyte body;
a first means for defining a thin flat space which has a predetermined diffusion resistance to restrict diffusion of a measurement gas to said first electrode, said thin flat space communicating with a measurement-gas space in which said measurement gas exists via a gas inlet aperture, said gas inlet aperture being formed through said electrochemical element in a plane normal to and intersecting a plane of said thin flat space, such that an inlet is formed in said thin flat space at a portion of said gas inlet aperture which intersects said thin flat space, said first electrode being substantially exposed to said measurement gas in said thin flat space, said means for defining a thin flat space including two opposed flat surfaces parallel to said plane of said thin flat space, said first electrode being disposed on a first of said two opposed flat surfaces and contacting a first portion of said first opposed flat surface, such that said first electrode is spaced a predetermined distance away from said inlet of said thin flat space in a direction parallel to said plane of the thin flat space, said measurement gas being introduced through said inlet into said thin flat space; and
a second means for substantially defining the thickness of said thin flat space, said second means comprising ceramic bridging means disposed in said thin flat space, said ceramic bridging means contacting a second portion of said first flat surface and the second surface of said two opposed flat surfaces, thereby bridging a gap between said two opposed flat surfaces, said ceramic bridging means being located away from the intersection of said gas inlet aperture and said thin flat space in said direction, and disposed in an area of said thin flat space corresponding to said predetermined distance, and thereby being in a non-contacting relationship with said first electrode.

26. An electrochemical element according to claim 25, wherein said means for defining a thin flat space and said ceramic bridging means comprise substantially the same material.

27. An electrochemical element according to claim 25, wherein said ceramic bridging means consists of a plurality of mutually spaced-apart ceramic members which are disposed at least in an area of said thin flat space adjacent to an inlet of said thin flat space through which said measurement gas is introduced into said thin flat space.

28. An electrochemical element according to claim 25, wherein said ceramic bridging means consists of a plurality of ceramic grains having a diameter which is substantially equal to the thickness of said thin flat space.

29. An electrochemical element according to claim 25, wherein said planar solid electrolyte body, and said first and second electrodes constitute a first electrochemical cell, and further comprising a second electrochemical cell which includes another planar solid electrolyte body, and another pair of electrodes, said thin flat space being formed between said first and second electrochemical cells.

30. An electrochemical element according to claim 25, further comprising a protective layer disposed between said bridging means and said first electrode, for preventing said bridging means from contacting said surface of said first electrode.

31. An electrochemical element, comprising:
a planar solid electrolyte body;
at least two electrodes including a first electrode and a second electrode which are disposed on said planar solid electrolyte body;
a first means for defining a thin flat space which has a predetermined diffusion resistance to restrict diffusion of a measurement gas to said first electrode, and which communicates with a measurement-gas space in which said measurement gas exists via a gas inlet aperture, said gas inlet aperture being formed through said electrochemical element in a plane normal to and intersecting a plane of said thin flat space, such that an inlet is formed in said thin flat space at a portion of said gas inlet aperture which intersects said thin flat space, said first electrode being spaced a predetermined distance away from said inlet of said thin flat space in a direction parallel to said plane of the thin flat space, said measurement gas being introduced through said inlet into said thin flat space, said first electrode being substantially exposed to said measurement gas in said thin flat space, said means for defining a thin flat space including two opposed flat surfaces parallel to said plane of said thin flat space; and
a second means for substantially defining the thickness of said thin flat space, said second means comprising a plurality of ceramic grains having a diameter substantially equal to a thickness of said thin flat space, and bridging a gap between said two opposed flat surfaces, said ceramic grains being located away from the intersection of said gas inlet aperture and said thin flat space in said direction and disposed in a portion of said thin flat space in a non-contacting relationship with said first and second electrodes, said ceramic grains being substantially mutually spaced apart from each other thereby permitting a flow of measurement gas through said portion of the thin flat space.

32. An electrochemical element, comprising:
a planar solid electrolyte body;
at least two electrodes including a first electrode and a second electrode which are disposed on said planar solid electrolyte body;

a first means for defining a thin flat space which has a predetermined diffusion resistance to restrict diffusion of a measurement gas to said first electrode, said thin flat space communicating with a measurement gas space in which said measurement gas exists via a gas inlet aperture, said gas inlet aperture being formed through said electrochemical element in a plane normal to and intersecting a plane of said thin flat space, such that an inlet is formed in said thin flat space at a portion of said gas inlet aperture which intersects said thin flat space, said first electrode being exposed to said measurement gas in said thin flat space, said means for defining a thin flat space including two opposed flat surfaces parallel to said plane of said thin flat space, said first electrode being disposed on a first of said two opposed flat surfaces and said second electrode being disposed on the second of said two opposed flat surfaces;

a first protective layer covering said first electrode on said first opposed flat surface;

a second protective layer covering said second electrode on said second opposed flat surface, said first and second protective layers further defining said thin flat space; and a second means for substantially defining the thickness of said thin flat space, said second means comprising ceramic bridging means disposed in said thin flat space such that said ceramic bridging means is located away from the intersection of said gas inlet aperture and said thin flat space in a direction parallel to said plane of the thin flat space, said ceramic bridging means contacting said first and second protective layers, thereby bridging a gap between said protective layers and substantially determining a thickness of said thin flat space.

* * * * *